United States Patent [19]

Ikegami et al.

[11] Patent Number: 4,736,058
[45] Date of Patent: Apr. 5, 1988

[54] PROSTACYCLINS AND PROCESS FOR PRODUCTION THEREOF

[75] Inventors: Shiro Ikegami, Hachioji; Seizi Kurozumi, Kokubunji, both of Japan

[73] Assignee: Teijin Limited, Osaka, Japan

[21] Appl. No.: 662,415

[22] PCT Filed: Jan. 26, 1984

[86] PCT No.: PCT/JP84/00018

§ 371 Date: Sep. 27, 1984

§ 102(e) Date: Sep. 27, 1984

[87] PCT Pub. No.: WO84/02902

PCT Pub. Date: Aug. 2, 1984

[30] Foreign Application Priority Data

Jan. 27, 1983 [JP] Japan ............................ 58-10577

[51] Int. Cl.[4] ............................................ C07C 177/00
[52] U.S. Cl. ...................................... 560/119; 544/173; 544/391; 546/108; 546/225; 548/200; 548/540; 549/417; 549/422; 549/466; 556/441; 560/56; 562/466; 562/501; 564/172; 564/188
[58] Field of Search ............... 560/119, 56; 562/466, 562/501; 564/172, 188; 556/441; 549/417, 422, 466; 548/540, 200; 546/225, 108; 544/173, 391

[56] References Cited

PUBLICATIONS

Koyama et al, Chem. Pharm. Bull., 32, 2866 (1984).
Sodoka et al, Chem. Letters, 579, (1984).
Torisawa et al, Chem. Letters, 1069 (1984).
Ogawa et al, Tet. Letters, 25, 1067 (1984).

Primary Examiner—Robert Gerstl
Attorney, Agent, or Firm—Sughrue, Mion, Zinn, Macpeak and Seas

[57] ABSTRACT

A novel prostacyclins expressed by the following formula (1)

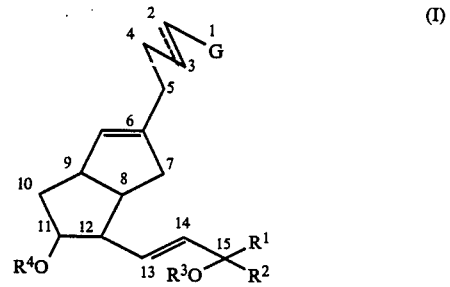

wherein a symbol ---- between the 2-position and 3-position indicates single bond or double bond; G indicates —$CO_2R^5$ or —$CONR^6R^7$ in which $R^5$ is a hydrogen atom, $C_1$-$C_{10}$ alkyl group, substituted or unsubstituted alicyclic group, substituted or unsubstituted phenyl ($C_1$-$C_2$) alkyl group, tri ($C_1$-$C_7$) hydrocarbon-silyl group, or one equivalent cation, $R^6$ and $R^7$ are identical or different and each representing a hydrogen atom, or $C_1$-$C_{10}$ alkyl group, or $R^6$ and $R^7$ are substituted or unsubstituted five to six-membered ring which may join together with a nitrogen atom to which they are linked and further contain a hetero atom; $R^1$ indicates a hydrogen atom, or methyl group; $R^2$ indicates an unsubstituted $C_3$-$C_8$ alkyl group substituted or unsubstituted alicyclic group, or substituted $C_1$-$C_5$ alkyl group substituted by substituents selected from phenyl, phenoxy, $C_1$-$C_6$ alkoxy and $C_5$-$C_6$ cycloalkyl group, which substituents may be substituted; and $R^3$ and $R^4$ are identical or different, each indicating a hydrogen atom, $C_2$-$C_7$ acyl group, tri ($C_1$-$C_7$) hydrocarbon-silyl group, or a group which forms an acetal linkage together with the oxygen atom of the hydroxyl group.

The prostacyclins has an excellent pharmacological activity such as platelet aggregation inhibiting action, and is extremely useful for medicine such as antithrombotic drug and antiarteriosclerotic drug.

5 Claims, No Drawings

PROSTACYCLINS AND PROCESS FOR PRODUCTION THEREOF

FIELD OF THE INVENTION

The present invention relates to prostacyclins and a process for the production thereof. More particularly, this invention relates to novel prostacyclins obtained by substituting oxygen atoms at 6- and 9-positions of prostaglandin $I_1$ with methine groups —HC= and a process for the production thereof.

BACKGROUND ART

Natural prostaglandin is a local hormone which is produced in vivo mainly by the inner walls of arteries and biologically it works as an important factor to control the cell function in a living body because of its strong physiological activities such as platalet aggregation inhibiting activity and vasodilating activity. Attempts have, therefore, been made to use it directly as pharmaceuticals (P. J. Lewis, J. O. Grady et al., "Clinical Pharmacology of Prostacyclin", Raven Press, N.Y., 1981). However, since natural prostacyclin has an enol ether bond, which is apt to be appreciably hydrolyzed, in its molecule, its action is readily paralysed under the neutral or acidic conditions, and accordingly it can not be a desirable compound to be used as medicine because of its chemical unstableness. To resolve such defect of natural prostacyclin, efforts have been directed to the development of chemically stable synthetic prostacyclin derivatives which have the same physiological activities as natural prostacyclin in Japan and abroad.

Especially, 6,9-(0)-methanoprostacyclin (Carbacyclin), which is a compound obtained by substituting the oxygen atom at the 6,9-positions or prostacyclin with a methylene group, is known as one of prostacyclins which are able to satisfy the chemical stableness to perfection (J. R. Vane et al., "Prostacyclin", pp. 31–41, Raven Press, N.Y., 1979) and is expected to work effectively as medicines. However, this 6,9(0)-methanoprostacyclin can not necessarily be regarded as a desirable compound in that it is inferior to natural prostacyclin in biological activity and it is not enough specific in action-selectivity. Beside this, nitroprostacyclin, a derivative obtained by substituting the oxygen atoms at the 6,9-positions with —N= group, is known as another type of stable prostacyclin and it is said that its biological activity is equal to that of natural prostacyclin (G. L. Bundy et al., Tetrahedron Letter, 1371 (1978) and W. Bartman et al., Tetrahedron Letter, 23, 3647 (1982)).

DISCLOSURE OF THE INVENTION

Having noticed the chemical structures of the chemically stable prostacyclin derivatives mentioned above, the inventors of the present invention have newly synthesized a prostacyclin derivative in which the oxygen atoms at the 6,9-positions are substituted with methine groups, —CH=, found that this type of prostacyclin derivative is chemically stable, excellent in action-selectivity, and useful as medicine, thus achieving this invention. This invention is to provide novel prostacyclins expressed by the following formula (I)

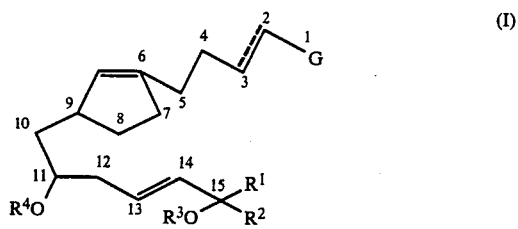

wherein a symbol ≈≈≈≈ between the 2-position and 3-position indicates single bond or double bond between the 2-position and 3-position; G indicates —$CO_2R^5$ or —$CONR^6R^7$, in which $R^5$ is a hydrogen atom, $C_1$–$C_{10}$ alkyl group, substituted or unsubstituted alicyclic group, substituted or unsubstituted phenyl ($C_1$–$C_2$) alkyl group, tri($C_1$–$C_7$) hydrocarbon-silyl group, or one equivalent of cation, $R^6$ and $R^7$ are identical or different and each represents a hydrogen atom or $C_1$–$C_{10}$ alkyl group, or $R^6$ and $R^7$ are substituted or unsubstituted five to six-membered rings which may join together with a nitrogen atom to which they are linked and further contain a hetero atom; $R^1$ indicates a hydrogen atom or methyl group; $R^2$ indicates an unsubstituted $C_3$–$C_8$ alkyl group, substituted or unsubstituted alicyclic group, or substituted $C_1$–$C_5$ alkyl group substituted by a substituent selected from phenyl, phenoxy, and $C_5$–$C_6$ cycloalkyl, which substituent may be substituted; and $R^3$ and $R^4$ are indentical or different, each indicating a hydrogen atom, $C_2$–$C_7$ acyl group, tri ($C_1$–$C_7$) hydrocarbon-silyl group, or a group which forms an acetal bond together with the oxygen atom of the hydroxyl group, and a process for the production thereof.

BEST MODE OF CARRYING OUT THE INVENTION

In the prostacyclins expressed by the aforementioned formula (I) of the present invention, the symbol ≈≈≈≈ between the 2-position and 3-position indicates single bond or double bond between the 2-position and 3-position.

In the aforementioned formula (I), G indicates —$CO_2R^5$ or —$CONR^6R^7$, in which $R^5$ is a hydrogen atom, $C_1$–$C_{10}$ alkyl group, substituted or unsubstituted phenyl group, substituted or unsubstituted alicyclic group, substituted or unsubstituted phenyl ($C_1$–$C_2$) alkyl group, tri($C_1$–$C_7$) hydrocarbon-silyl group, or one-equivalent of cation. As examples of a ($C_1$–$C_{10}$) alkyl group, such straight-chain or branched groups as methyl, ethyl, n-propyl, iso-propyl, n-butyl, sec-butyl, tert-butyl, n-pentyl, n-hexyl, n-heptyl, n-octyl, n-nonyl, and n-decyl, for instance, may be mentioned.

As for substituents of substituted phenyl group, a halogen atom, hydroxy group, $C_2$–$C_7$ acyloxy group, $C_1$–$C_4$ alkyl group which may be substituted by a halogen atom, $C_1$–$C_4$ alkoxy group which may be substituted with a halogen atom, nitryl group, carboxyl group, and ($C_1$–$C_6$) alkoxycarbonyl group may be mentioned as desirable ones. As halogen atom cited here, there are fluorine, chlorine, and bromine, of which flourine and chlorine are desirable. As $C_2$–$C_7$ acyloxy group, acetoxy, propionyloxy, n-butyryloxy, iso-butyryloxy, n-valeryloxy, iso-valeryloxy, caproyloxy, enanthyloxy, and benzoyloxy may be mentioned.

As $C_1$–$C_4$ alkyl group which may be substituted by a halogen atom, methyl, ethyl, n-propyl, iso-propyl, n-butyl, chloromethyl, dichloromethyl, and trifluoromethyl may be mentioned as desirable ones. As $C_1$–$C_4$ alkoxy group which may be substituted with a halogen atom, methoxy, ethoxy, n-propoxy, iso-propoxy, n-butoxy, chloromethoxy, dichloromethoxy, and trifluoromethoxy may be mentioned as desirable ones. As ($C_1$–$C_6$) alkoxycarbonyl group, methoxycarbonyl, ethoxycarbonyl, butoxycarbonyl, and hexyloxycarbonyl may be mentioned.

The substituted phenyl group may have one to three, desirably one, substituent group as mentioned above.

As substituted or unsubstituted alicyclic group, such $C_5$–$C_8$ alicyclic groups, desirably $C_5$–$C_6$ alicyclic group, that are substituted by any of the same substituent groups as mentioned above or unsubstituted, saturated or unsaturated, as cyclopentyl, cyclohexyl, cyclohexenyl, cycloheptyl, and cyclooctyl may be mentioned.

As substituted or unsubstituted phenyl ($C_1$–$C_2$) alkyl group, benzyl, α-phenetyl, and β-phenetyl, in which said phenyl group is substituted by the same substituent group as mentioned above or unsubstituted, may be mentioned.

As tri ($C_1$–$C_7$)hydrocarbon-silyl group, such tri ($C_1$–$C_4$) alkylsilyl as trimethylsilyl, triethylsilyl, and t-butyldimethylsilyl groups, such diphenyl ($C_1$–$C_4$) alkylsilyl as t-butyldiphenylsilyl group, tribenzylsilyl group, and dimethyl-(2,4,6-tri-t-butylphenyloxy)silyl group may be mentioned as desirable ones. As one-equivalent of cation, such alkali metal cations as Na$^+$ and K$^+$, such divalent or trivalent metal cations as ½ Ca$^{2+}$, ½ Mg$^{2+}$, and ⅓ Al$^{3+}$, and such ammonium cations as ammonium ion and tetramethylammonium ion may be mentioned.

$R^6$ and $R^7$ of —CONR$^6$R$^7$ are identical or different, each representing a hydrogen atom or $C_1$–$C_{10}$ alkyl group, or $R^6$ and $R^7$ are substituted or unsubstituted five to six-membered rings which may join together with a nitrogen atom to which they are linked and further contain a hetero atom. Here, as $C_1$–$C_{10}$ alkyl group, the same alkyl groups as mentioned before may be mentioned. As the substituent groups in the abovementioned substituted or unsubstituted rings, the same substituent groups as mentioned above may be mentioned, and as hetero atoms, nitrogen, sulfur, and oxygen atoms may be mentioned. As the abovementioned rings, 1-pyrrolidyl, thiazolyl, 1-piperidyl, morpholyl, piperazyl, and 5,6-dihydrophenanthridyl groups may be mentioned.

As for G, —CO$_2$R$^5$, in which R$^5$ is a hydrogen atom, $C_1$–$C_{10}$ alkyl group, or alkali metal cation, is desirable, and it is especially desirable when R$^5$ is a carboxy group or methyl group.

$R^1$ is a hydrogen atom or methyl group and the hydrogen atom is preferable.

$R^2$ is an unsubstituted $C_3$–$C_8$ alkyl group; substituted $C_1$–$C_5$ alkyl group substituted by a substituent selected from phenyl, phenoxy, $C_1$–$C_6$ alkoxy and $C_5$–$C_6$ cycloalkyl, which substituent may be substituted; or substituted or unsubstituted alicyclic group. Said unsubstituted $C_3$–$C_8$ alkyl group may be either of straight-chain and branched. For instance, n-pentyl, n-hexyl, 2-methyl-1-hexyl, 2-methyl-2-hexyl, n-heptyl, and n-octyl may be mentioned and n-pentyl, n-hexyl, 2-methyl-1-hexyl, 2-methyl-1-hexyl, and 1-methyl-1-pentyl are desirable. Substituted $C_1$–$C_5$ alkyl group may be either straight-chain or branched. For instance, methyl, ethyl, n-propyl, iso-propyl, n-butyl, sec-butyl, t-butyl, and n-pentyl may be mentioned. These alkyl groups are substituted by a phenyl group; phenoxy group; such $C_1$–$C_6$ alkoxy groups as methoxy, ethoxy, n-propoxy, iso-propoxy, n-butoxy, iso-butoxy, t-butoxy, n-pentoxy, and n-hexoxy; and such $C_5$–$C_6$ cycloalkyl groups as cyclopentyl and cyclohexyl. These substituent may also be substituted by any of the substituents mentioned as the substituents of the substituted phenyl group of $R^5$.

As substituted $C_1$–$C_5$ alkyl group, $C_1$–$C_2$ alkyl group substituted by a phenoxy or phenyl group which may further be substituted by a fluorine atom, chlorine atom, methyl, ethyl, or trifluoromethyl group; and propoxymethyl, ethoxyethyl, propoxyethyl, butoxymethyl, methoxypropyl, 2-ethoxy-1,1-dimethylethyl, and propoxydimethylmethyl, or cyclohexylmethyl, cyclohexylethyl, cyclohexyldimethylmethyl, and 2-cyclohexyl-1,1-dimethylethyl are desirable.

As substituted or unsubstituted alicyclic group, the same ones as those mentioned in the case of $R^5$ may be mentioned again. As for $R^2$, n-pentyl, 2-methyl-1-hexyl, 1-methyl-1-pentyl, cyclopentyl and cyclohexyl groups are especially desirable.

$R^3$ and $R^4$ are identical or different, each indicating a hydrogen atom, $C_2$–$C_7$ acyl group, tri ($C_1$–$C_7$) hydrocarbon-silyl group, or a group which forms an acetal bond together with the oxygen atom of the hydroxyl group.

As $C_2$–$C_7$ acyl group, acetyl, propionyl, n-butyryl, iso-butyryl, n-valeryl, iso-valeryl, caproyl, enanthyl, and benzoyl may, for instance, be mentioned.

Of these, such $C_2$–$C_6$ aliphatic acyl groups as acetyl, n- or iso-butyryl, caproyl, and benzoyl are desirable.

As tri ($C_1$–$C_7$) hydrocarbon-silyl group, the same ones as those mentioned in the case of $R^5$ may again be mentioned.

As examples of a group which forms an acetal bond together with the oxygen atom of the hydroxyl group, methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl, 4-(4-methoxy-tetrahydropyranyl) group, or 6,6-dimethyl-3-oxa-2-oxo-bicyclo [3,1,0] hex-4-yl may be mentioned. Of these, 2-tetrahydropyranyl, 2-tetrahydrofuranyl, 1-ethoxyethyl, 2-methoxy-2-propyl, (2-methoxyethoxy)methyl, 4-(4-methoxytetrahydropyranyl) group, 6,6-dimethyl-3-oxa-2-oxo-bicyclo [3,1,0] hex-4-yl group, and dimethyl (2,4,6-tri-t-butylphenyloxy) silyl group are especially desirable.

As for $R^3$ or $R^4$, a t-butyldimethylsilyl group, 2-tetrahydropyranyl group, acetyl group, 1-methoxy-1-methylethyl group, 4-(4-methoxytetrahydropyranyl) group, 6,6-dimethyl-3-oxa-2-oxo-bicyclo [3,1,0] hex-4-yl group, and dimethyl (2,4,6-tri-t-butylphenyloxy)silyl group are especially desirable among those mentioned above.

Desirable examples of prostacyclins provided by the present invention are shown below specifically.

(100) 9(0)-methano-Δ$^{6(9)}$-prostaglandin I$_1$
(102) 16,17,18,19,20-pentanor-15-cyclopentyl-9(0)-methano-Δ$^{6(9)}$-prostaglandin I$_1$
(104) 16,17,18,19,20-pentanor-15-cyclohexyl-9(0)-methano-Δ$^{6(9)}$-prostaglandin I$_1$
(106) 17,18,19,20-tetranor-16-cyclohexyl-9(0)-methano-Δ$^{6(9)}$-prostaglandin I$_1$
(108) 17,18,19,20-tetranor-16-cyclopentyl-9(0)-methano-Δ$^{6(9)}$-prostaglandin I$_1$
(110) 17,18,19,20-tetranor-16-phenoxy-9(0)-methano-Δ$^{6(9)}$-prostaglandin I$_1$
(112) 17,18,19,20-tetranor-16-(p-fluorophenoxy)-9(0)-methano-Δ$^{6(9)}$-prostaglandin I$_1$ (114) 17,20-dimethyl-9(0)-methano-$\Delta^{6(9)}$-prostaglandin $I_1$
(116) 16-methyl-9(0)-methano-$\Delta^{6(9)}$-prostaglandin $I_1$
(118) 15-methyl-9(0)-methano-$\Delta^{6(9)}$-prostaglandin $I_1$
(120) 16,16-dimethyl-9(0)-methano-$\Delta^{6(9)}$-prostaglandin $I_1$
(122) methyl ester of (100)
(124) methyl ester of (102)
(126) methyl ester of (104)
(128) methyl ester of (106)
(130) methyl ester of (108)
(132) ethyl ester of (110)
(134) ethyl ester of (112)
(136) propyl ester of (114)
(138) butyl ester of (116)
(140) sodium salt of (100)
(142) sodium salt of (102)
(144) sodium salt of (114)
(146) sodium salt of (116)
(148) 11,15-bis-(t-butyldimethylsilyl)ether of (122)
(150) 11,15-bis-(t-butyldimethylsilyl)ether of (124)
(152) 11,15-bis-(t-butyldimethylsilyl)ether of (126)

Prostacyclins of the present invention are produced by subjecting epoxyprostacyclins which are expressed by the following formula (II)

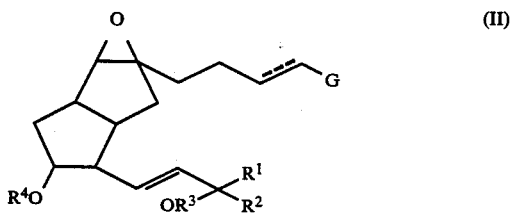
(II)

wherein a symbol ===== between the 2-position and 3-position, G, $R^1$, $R^2$, $R^3$, and $R^4$ are as defined hereinbefore,
to the treatment with a halogenide of alkali metal and acid anhydride, and then to the reductive reaction by use of an alkaline earth metal, followed by a deprotecting reaction, hydrolyzing reaction, or salt-forming reaction, if required.

The epoxyprostacyclins of the aforementioned formula (II), which are the material compounds in this invention, are novel compound and are produced according to a manufacturing process described hereinafter.

Epoxyprostacyclins are first treated with a halogenide of alkali metal and acid anhydride. As halogenides of alkali metal, there are such compounds that are expressed by the following formula (III)

MX (III)

wherein M indicates an alkali metal and X indicates a halogen atom.
M represents such an alkali metal as lithium, sodium, and potassium, and X represents such a halogen atom as chlorine, bromine, and iodine. As halogenide of alkali metal, sodium iodide, potassium iodide, and sodium bromide are desirable and sodium iodide is especially desirable.

As acid anhydride, acetic anhydride, trifluoroacetic anhydride, propionic anhydride, α,α'-difluoropropionic anhydride, butyric anhydride, and mixed acid anhydride of acetic acid trifluoroacetic acid may be mentioned, of which trifluoroacetic anhydride is desirable.

Desirable examples of reaction solvent include such ethers as diethyl ether, tetrahydrofuran (THF), and dioxane.

A halogenide of alkali metal may be used desirably in an amount of 0.5–30 moles, most desirably 4–10 moles, per mole of epoxyprostacyclin, the starting material compound, and an acid anhydride desirably in an amount of 0.1–1.5 moles, most desirably 0.2–0.5 mole, per mole of expoxyprostacyclin. The reaction temperature is desirably from $-30°$ C. to $100°$ C., most desirably from $10°$ C. to $30°$ C. It is deemed that the treatment of epoxyprostacyclin with a halogenide of alkali metal and acid anhydride at first forms an acid halide, which then reacts with the epoxy structure of epoxyprostacyclin.

The reaction product is then reduced with an alkaline earth metal. As alkaline earth metals, zinc and copper may be mentioned and zinc is especially desirable. The amount of an alkaline earth metal to be used is desirably 1–50 moles, most desirably 10–30 moles per mole of epoxyprostacyclin. It is desirable to control the reaction temperature in the range from $0°$ C. to $100°$ C., especially desirable when kept between $40°$ C. and $70°$ C. It is advisable to carry out the reduction reaction with an alkaline earth metal in succession to the aforementioned treatment with a halogenide of alkali metal and acid anhydride in the same reaction system.

The posttreatment of the reaction mixture thus obtained may be conducted according to the any of the methods commonly adopted. For example, an organic solvent, which is hardly soluble in water, such as hexane, pentane, petroleum ether, and ethyl ether is added to the obtained reaction mixture to make an organic mixture, or otherwise such an organic solvent is added to the reaction mixture after it is concentrated under reduced pressure to obtain a likely organic mixture. The obtained organic mixture is washed with a saline solution and dried over such a drying agent as magnesium sulfate anhydride, sodium sulfate anhydride, and potassium carbonate anhydride and then the organic solvent is removed therefrom under reduced pressure to obtain a crude reaction product. The obtained crude product may be refined, as desired, according to such a refining method as column chromatography, thin layer chromatograph, liquid chromatography, and, preferably, column chromatograph which is kept in a basic atmosphere with an amine such as trimethylamine. The refined product may further be subjected to a deprotecting reaction, hydrolyzing reaction, or salt-forming reaction, if required.

The removal of a hydroxyl-protecting group (deprotecting reaction) is carried out satisfactorily by use of acetic acid, pyridinium salt of p-toluenesulfonic acid, or cation-exchange resin as a catalyst in the reaction solvent such as water, tetrahydrofuran, ethyl ether, dioxane, acetone, and acetonitrile, in case where the protecting group is a group which forms an acetal bond together with the oxygen atom of hydroxyl group. The reaction is usually carried out at a temperature ranging from $-78°$ C. to $+30°$ C. for 10 minutes to 3 days. In case where the protecting group is a tri ($C_1$-$C_7$) hydrocarbon-silyl group, the reaction is carried out in the presence of acetic acid, tetrabutylammonium fluoride, cesium fluoride, desirably either one of the last two of them (and that more desirably in the coexistence of such a basic compound as triethylamine), in the same reaction solvent as mentioned above (desirably other than water) at the same temperature and for the same period of time as above. In case where the protecting group is an acyl group, the reaction can be effected by carrying out the hydrolysis in an aqueous solution of sodium hydroxide, potassium hydroxide, or calcium hydroxide; or a mixture of water and alcohol; or methanol or ethanol solution of sodium methoxide, potassium methoxide, or sodium ethoxide.

The hydrolysis reaction of the ester group of carboxyl group is carried out by use of such an enzyme as lipase in water or a solvent containing water at a temperature ranging from −10° C. to +60° C. for about 10 minutes to 24 hours.

The product obtained in the deprotecting reaction or hydrolysis reaction can be refined according to the same refining methods as mentioned above.

The compound which has a carboxyl group formed as the result of the abovementioned reaction of removing the protecting group may be subjected to the salt-forming reaction, if required, to give a corresponding carboxylic salt. The salt-forming reaction is known per se, and can be carried out by neutralizing the reaction product with a basic compound such as sodium hydroxide, potassium hydroxide, and sodium carbonate approximately equivalent in amount to the carboxylic acid, or ammonia, trimethylamine, monoethanolamine, and morpholine according to the ordinary method. In this way, prostacyclins of this invention are obtained.

The epoxyprostacylins which are used as material compound in the process proposed by this invention can be obtained by the following reaction.

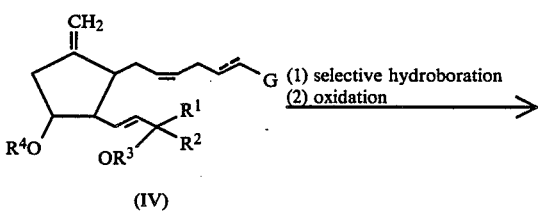

(IV)

(V)

(VI)

-continued (VII)

(II)

The compound of the aforementioned formula (IV) is a known compound and can be produced according to the methods described in the documents, Prostaglandins, 17, 657 (1979) and U.S. Pat. No. 4,137,403.

The compound of formula (V) can be obtained by subjecting the compound (IV) to the selective hydroboration, followed by oxidation conducted under the alkaline conditions. As the selective hydroboration agent, bulky reagents as 9-borabicyclo [3,3,1] nonane (9-BBN), texylborane, and dinosokanhonylborane are used desirably and the reaction is usually carried out in tetrahydrofuran or ethers while being cooled with ice. The reaction solution is then oxidized under the alkaline conditions to be lead to the product (V). In the oxidative reaction under the alkaline conditions, a 5M sodium hydroxide aqueous solution and aqueous hydrogen peroxide are most desirably used. The reaction is usually conducted in an ice bath.

The compound (VI) is obtained by allowing the compound (V) to react with a halogenide, then by treating the reaction product with a basic compound, and further by treating with an acidic compound. As the halogenides, iodine, bromine, potassium iodide, and N-bromosuccinimide are desirable, and as the reaction solvents, methylene chloride, chloroform, carbon tetrachloride, and diethyl ether are used. The reaction is usually carried out with cooling with ice.

The reaction with a halogenide convert the compound (V) to a halogenated ether expressed by the following formula.

Thus converted product is now treated with a basic compound. As the basic compounds, such amines as 1,5-diazabicyclo [5,4,0] undecene-5 (DBU), and 1,5- diazabicyclo [4,3,0] nonene-5,1,4-diazabicyclo [2,2,0] octane are desirable. As the reaction solvents, benzene, toluene, and xylene may be mentioned as desirable ones. It is desirable to control the reaction temperature ranging from 10° C. to 60° C. The obtained reaction product is then treated with an acidic compound. As the acidic compound, hydrochloric acid, sulfuric acid, hydrobromic acid, and p-toluenesulfonic acid are desirable ones. It is advisable to keep the reaction temperature between 30° C. and 80° C. The halogenated ethers are converted to the compound (VI) as shown by the following formulas when subjected to the treatments with a basic compound and also with an acidic compound as mentioned above.

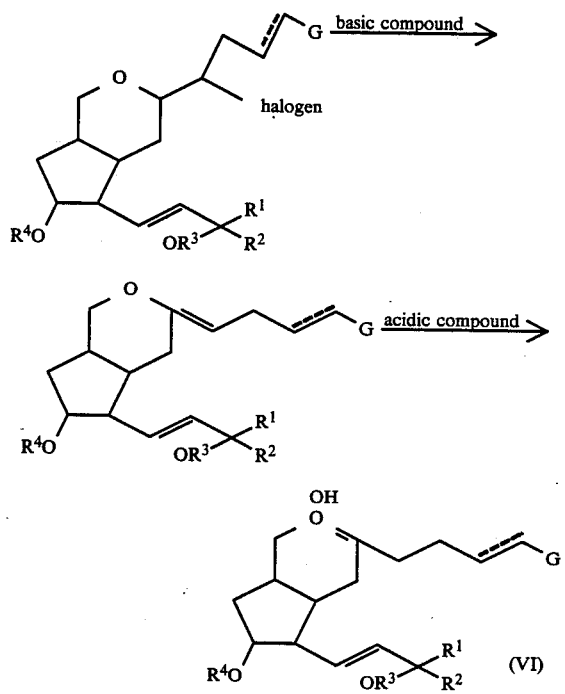

The compound (VII) can be obtained by coverting the hydroxymethyl group at the 9-position of the compound (VI) to aldehyde by oxidation, and further allowing this formyl group to condense with the carbonyl group at the 6-position.

In oxidizing the hydroxymethyl group, it is especially advisable to use an oxidizing agent of aminesulfur trioxide.pyridin complex-dimethyl sulfoxide system. The reaction usually takes effect at the temperature ranging from 10° C. to 40° C. It is desirable to use the oxidizing agent in such an excessive amount of 2 to 100 moles per mole of the compound (VI). A compound expressed by the following formula is formed intermediately.

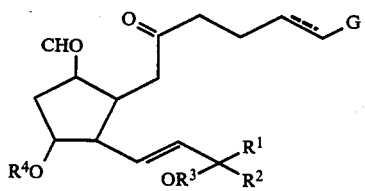

Then this intermediate compound is treated in the Lewis acid-alkaline earth metal system to obtain the compound (VII). As Lewis acid to be used in the reaction, there are titanium (II) chloride and tin (II) chloride. As the alkaline earth metal, zinc is most desirably used. As the reaction solvent, such ethers as tetrahydrofuran and ethers are used. The reaction is usually carried out with cooling in ice-cold water.

Epoxyprostacyclins represented by the compound (II) can be obtained by allowing the compound (VII) to react with a halogenide of organic sufonic acid, followed by the treatment with a basic compound.

As the halogenide of organic sulfonic acid, there are, for instance, methanesulfonyl chloride, ethanesulfonyl chloride, n-butanesulfonyl chloride, trifluoromethanesulfonyl chloride, and p-toluenesulfonyl chloride. It is advisable to use such basic compounds as triethylamine, 4-dimethylaminopyridine, and diisopropylcyclohexylamine together with said halogenide of organic sulfonic acid. Such hydrocarbon halogenides as dichloromethane, chloroform, and carbon tetrachloride are desirable reaction solvent to be used here. It is halogenide of organic sulfonic acid is used in the same number of molecules as the compound (VII). It is desirable to use the halogenide of organic sulfonic acid in the same number of molecules as the compound (VII) and more than two moles of the basic compound. Benzene, toluene, and xylene are among the desirable solvent in this reaction. It is advisable to keep the reaction temperature ranging from 10° C. to 60° C. According to the process mentioned above, epoxyprostacyclins of formula (II), which is the material compound of the present invention, are obtained.

The marvel is that the novel prostacyclins of formula (I) provided by this invention have a very strong biological activities. For example, it has been proved that $9(0)$-methano-$\Delta^{6(9)}$-prostaglandin $I_1$ not only inhibits the platelet aggregation of rabbits induced by ADP with the administration of $IC_{50}=0.0054$ μg/ml but also has a cell protecting action with $10^{-6}M$ against cell lethal action on the epithelial cells of bone of rabbits at pH 3. The compounds of this invention have a remarkably strong platelet aggregation inhibiting action as compared with other pharmacological actions such as hypotensive action, etc. and it may be said that they are compounds having a high action-selectivity.

From the facts described above, it may be asserted that compounds of this invention are extremely useful in that they can be applicable to the preparation of antithrombotic drug, antiarteriosclerotic agent, and antimetastatic substance for cancer, and that they can also be expected to have their application in the making of untiulcer agent, and drug for asthma. Furthermore, intermediate products, which are formed intermediately during the process of making the final products, are expected not only to have a strong biological activities by themselves, but also to be led to new prostaglandins, thus attaching a deep industrial significance to this invention.

The following Examples illustrate more specifically, but not in any way limit, the present invention.

EXAMPLE 1

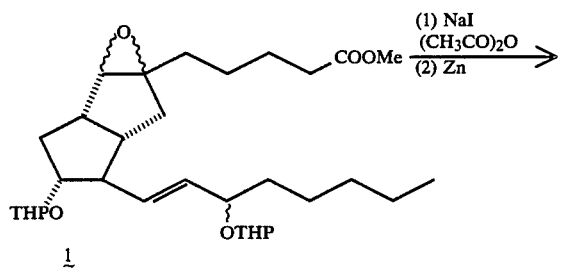
1

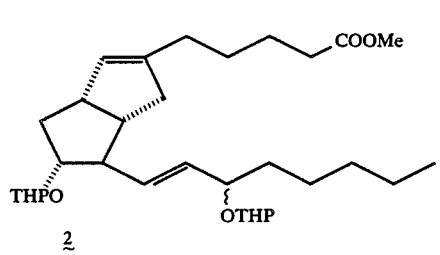
2

To a dry tetrahydrofuran (5 ml) were added with stirring NaI (300 mg, 2 mmol) and trifluoroacetic anhydride (0.0765 ml, 0.5 mmol), and the mixture was stirred for 10 minutes to form $CF_3COI$ and turn dark yellow. To the resulting solution was added dropwise by a syringe a solution of epoxide (1) (140 mg, 0.255 mmol) in THF (3 ml). After the mixture was stirred for 15 minutes, it could be confirmed by TLC (ether:petroleum ether=1:) that the starting material was used out, the UV-absorbing product was obtained. To the reaction mixture was added all at once a superfluous zinc powder (350 mg, 5.38 mmol) at room temperature, and the mixture was stirred for 1 hour at room temperature. The mixture was stirred for a further 1 hour at 60°~65° C. After the reaction mixture was cooled to room temperature, to the mixture were added ether (about 80 ml) and Florigil. The resulting inorganic precipitate was removed by filtration through Florigil. The precipitate was washed with ether (30 ml×2), and the combined ether layer was washed with a saturated aqueous solution of sodium hydrogen carbonate and a saturated aqueous solution of sodium chloride, dried over anhydrous magnesium sulfate, and concentrated. The residue was chromatographed on a silica gel column (ether:petroleum ether=1:). The desired olefine 2 (60 mg, 44.2%) was collected as yellow oil from less polar part and the starting material epoxide 1 (60 mg, 43%) was collected from more polar part.

Product:

IR (neat): 2925, 2850, 1735, 1440 $cm^{-1}$.

NMR ($\delta$, $CDCl_3$): 5.45 (m, 2H), 5.26 (br.s, 1H), 4.68 (m, 2H), 4.20-3.70 (m, 4H), 3.68 (s, 3H), 3.65-3.25 (m, 2H), 2.95 (m, 1H), 0.90 (m, 3H).

Mass (m/e): 501 (M—$OCH_3$), 345; (m/e) 501.3538 (calcd for $C_{31}H_{49}O_5$, 501.3567, M—$OCH_3$).

EXAMPLE 2

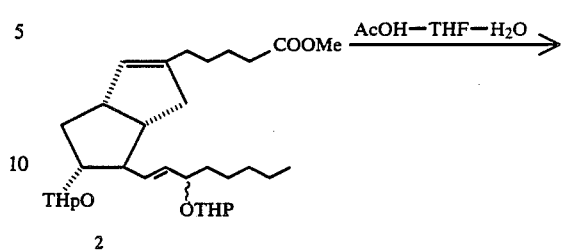
2

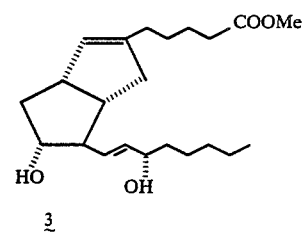
3

To a tetrahydropyranyl compound 2 (24 mg, 0.045 mmol) was added a mixture (1 ml) of acetic acid, water and tetrahydrofuran (3:1:1) at room temperature. The mixture was heated, and was stirred for 1 hour at 50°–55° C. It could be confirmed by TLC (ether) that the starting material was used out and two high polar products were formed. The reaction mixture was cooled to room temperature, diluted with ether (about 30 ml), and neutralized with an excess of a saturated aquous solution of sodium hydrogen carbonate (about 10 ml). The water layer was extracted with ether (about 80 ml), and the extracts were combined, washed with a saturated aqueous solution (5 ml×2) of sodium chloride, dried over anhydrous magnesium sulfate, and concentrated. The residue (25 mg) was purified by silica gel thin-layer chromatography (0.25 mm×20 cm20 cm×1, either). The desired 15α-diolester compound 3 (9.0 mg, 55.8%) was collected as colorless oil from more polar parts (Rf=0.13, ether), and 15β-diolester compound (3.1 mg, 22.3%) was collected as colorless oil from less polar parts (Rf=0.31, ether)

15α-compound:

IR (neat): 3350, 2925, 2850, 1740, 1435, 1200, 1020 $cm^{-1}$.

NMR ($\delta$, $CDCl_3$): 5.55 (m, 2H), 5.30 (brs, 1H), 4.25-3.95 (m, 2H), 3.68 (s, 3H), 3.90-3.55 (m, 2H), 3.20-2.80 (m, 2H), 0.90 (m, 3H).

Mass (m/e): 346 (M—$H_2O$), 328, 302 (m/e) 346.2516 (calcd for $C_{22}H_{34}O_3$, 346.2499, M—$H_2O$).

15β-compound:

IR (neat): 3350, 1740 $cm^{31\ 1}$.

NMR ($\delta$, $CDCl_3$): 5.50 (m, 2H), 5.31 (brs, 1H), 4.3-3.9 (m, 2H), 3.65 (s, 3H).

Mass (20 eV, m/e): 346 ($M^+$-18).

EXAMPLE 3

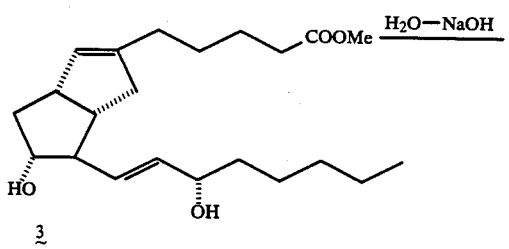

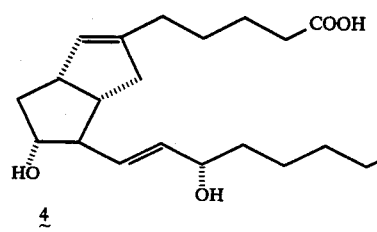

An ester compound 3 (9 mg, 0.025 mmol) was dissolved in a mixture (1 ml) of tetrahydrofuran and water (1:1) at room temperature, and to the solution was added 5M—NaOH (0.2 ml). The mixture was stirred over night at room temperature. The reaction mixture was heated at 40° C. and stirred for a further 20 hours. It could be confirmed by TLC (ether) that the starting material was used out. The reaction mixture was cooled to room temperature, diluted with ether (about 20 ml), neutralized with 10% HCl and pH4 buffer, and adjusted to pH 3-4. The resulting mixture was extracted with ethyl acetate (40 ml and 20 ml), and organic layers were combined, washed with a saturated aqueous solution of sodium chloride (3 ml×2), dried over anhydrous magnesium sulfate, and concentrated. The residue was purified by silica gel capillary column (ether acetate:methanol=15:1) to give a carboxylic acid compound 4 (9(o)-methano-$\Delta^{6(9)}$-prostaglandin $I_1$) (8 mg, 92%).

IR (neat): 3350, 2910, 2850, 1700, 1450, 1250 cm$^{-1}$.
NMR ($\delta$, CDCl$_3$): 5.55 (m, 2H), 5.30 (brs, 1H), 4.55 (m, 3H), 4.10 (m, 1H), 3.75 (m, 1H), 3.00 (m, 1H), 2.75-2.20 (m, 4H), 2.20-1.90 (m, 2H).
Mass (Cl, NH$_3$): m/3, 368 (M$^+$+NH$_4$).
mp: 73-790.
[$\alpha$]$_D$: 16.0° (C, 0.25, MeOH).

EXAMPLE 4

16,17,18,19,20-Pentanor-15-cyclopentyl-9(0)-methano-$\Delta^{6(9)}$-prostaglandin $I_1$ methyl ester was obtained in the same way as Examples 1 and 2.

IR (CHCl$_3$): 3600, 3400, 2950, 2855, 1730, 1435, 970.
NMR ($\delta$, CDCl$_3$): 5.70-5.55 (m, 2H, olefinic), 5.30 (brs, 1H, olefinic), 3.70 (s, 3H, OMe).
MSm/e: 362 (M$^+$), 344 (M$^+$—H$_2$O).

EXAMPLE 5

16,17,18,19,20-Pentanor-15-cyclopentyl-9(0)-methano-$\Delta^{6(9)}$-prostaglandin $I_1$ methyl ester (7 mg) was dissolved in a mixture of methanol (1.5 ml) and water (0.5 ml). To the solution was added dropwise 5M—NaOH (0.2 ml) at room temperature, and the mixture was stirred for 2 hours. The reaction mixture was treated in a same way as Example 3 to give 16,17,18,19,20-pentanor-15-cyclopentyl-9(0)-methano-$\Delta^{6(9)}$-prostaglandin $I_1$ (5 mg, 75.6%).

IR (CHCl$_3$): 3400, 2950, 2865, 1705, 1470, 970.
NMR ($\delta$, CDCl$_3$): 5.60-5.40 (m, 2H, olefinic), 5.20 (brs, 1H, olefinic), 4.30-3.30 (m, 9H).
m.p.: 115°-116° C.

EXAMPLE 6

16-Methyl-9(0)-methano-$\Delta^{6(9)}$-prostalgandin $I_1$ methyl ester was obtained in a same way as Example 1 and 2.

IR (CHCl$_3$): 3600, 3400, 2920, 2850, 1720, 1450, 1430, 1230, 965.
NMR ($\delta$, CDCl$_3$P): 5.75-5.55 (m, 2H, olefinic), 5.30 (bs, 1H, olefinic), 3.75 (s, 3H, OMe), 1.10-0.80 (m, 6H).
MS m/e: 378 (M$^+$), 360 (M$^+$—H$_2$O).

EXAMPLE 7

16-Methyl-9(0)-methano-$\Delta^{6(9)}$-prostaglandin $I_1$ methyl ester (7 mg) was dissolved in a mixture of methanol (1.5 ml) and water (0.5 ml). To the solution was added dropwise with stirring 5M—NaOH (0.2 ml) at room temperature, and the mixture was stirred for 2 hours at room temperature. The reaction mixture was diluted with a small amount of ether, and neutrized with 1N—HCl (1 ml) to adjust pH 1-2. To the mixture was added ether, and the ether layer was washed with a small amount of a saturated aqueous solution of sodium chloride, dried over anhydrous magnesium sulfate, and concentrated. The residue was purified by silica gel short column (ethylacetate:methanol=15:1) to give 16-methyl-9(0)-methano-$\Delta^{6(9)}$-prostaglandin $I_1$ (5 mg, 76.3%) as yellow oil.

IR (CHCl$_3$): 3350, 2925, 2850, 1705, 1450, 965.
NMR ($\delta$, CDCl$_3$): 5.75-5.45 (m, 2H, olefinic), 5.35 (brs, 1H, olefinic), 5.00-4.50 (m, 3H, OH), 1.10-0.80 (m, 6H, CH$_3$).

REFERENTIAL EXAMPLE 1

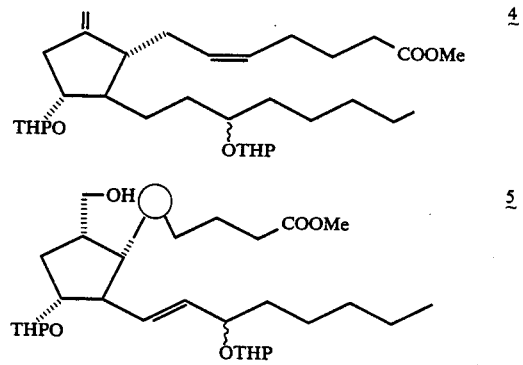

A 9-methylene compound 4 (300 mg, 0.56 mmol) was dissolved in a dry THF (3 ml), and the solution was cooled to 0° C. on ice-bath. To the solution was added dropwise by a syringe a solution (6 ml) of 9-BBN (Aldrich. 0.38M, 2.28 mmol) in THF, and the mixture was stirred for 3 hours at 0° C. To the reaction mixture were added 5M-NaOH (1 ml) and 31% H$_2$O$_2$ (2 ml), and the mixture was heated to room temperature. The mixture was reacted for 1 hour at room temperature and for a further 1 hour at 40° C.-50° C. The reaction mixture was cooled at room temperature, and diluted with ether (about 50 ml). To the solution was added a saturated aqueous solution of sodium thiosulfate, and the mixture was stirred until KI starch-paper didn't toun blue. The organic layer was separated, and the water layer was extracted with ether (30 ml). The ether extracts were combined, washed with 10% HCl, a saturated aqueous solution of sodium hydrogen carbonate and a saturated aqueous solution of sodium chloride, dried over anhydrous magnesium sulfate, and concentrated. The residue was chromatographed on a silica gel column (ethyl acetate:petraleum ether =1:2) to give alcohol compound 5 (200 mg, 64.%) as colorless oil.

IR (neat): 3450, 2950, 2850, 1740, 1440, 1020 cm$^{-1}$.

NMR ($\delta$, CDCl$_3$): 5.40 (m, 4H), 4.65 (m, 2H), 3.65 (m, 2H), 9.90 (m, 2H).

Mass (m/e): 532 (M—H$_2$O), 448, 430, 417, 400, 345.

REFERENTIAL EXAMPLE 2

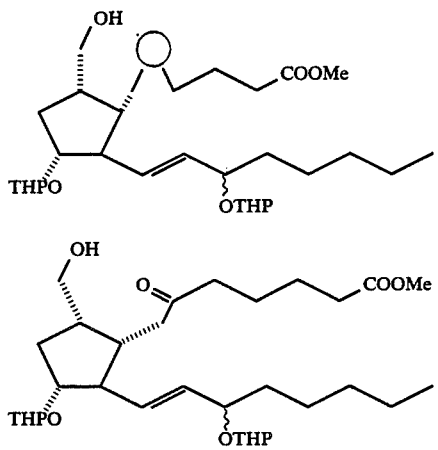

An alcohol compound 5 (233 mg, 0.42 mmol) was dissolved in a mixture of CH$_2$Cl$_2$ (5 ml) and a saturated aqueous solution (5 ml) of sodium hydrogen carbonate, and the solution was cooled to 0° C., and then iodine (220 mg, 0.87 mmol) was added as solid all at once. The dark red mixture was stirred for 30 minutes at 0° C., and it was confirmed by TLC (ethyl acetate:petroleum=1:2) that the starting material disappeared. The reaction mixture was diluted with a small amount of ether (about 20 ml), and a saturated aqueous solution (about 5 ml) was added, and then the mixture was stirred until the dark red died away. To the reaction mixture was added ether (about 20 ml), and the mixture was washed with a saturated aqueous solution of sodium chloride, dried over anhydrous magnesium sulfate, and concentrated to give iodine ether (230 mg) as light yellow oil. The product was dried with azeotropy together with benzene several times, and dissolved in dry toluene (2.5 ml). To the mixture was added DBU (0.5 ml) by syringe all at once. The mixture was heated to 60° C., and then stirred for 6 hours at 60° C. It was confirmed by TLC (ethyl acetate:petroleum=1:2) that the starting material disappeared. The reaction mixture was cooled to room temperature, and diluted with ether (20 ml). To the mixture was added 10% HCl (5 ml), and the mixture was stirred for a while. After the organic layer became clearness, ether (50 ml) was added, and washed with 10% HCl until the water layer became acid. The organic layer was washed with a saturated aqueous solution of sodium hydrogen carbonate and saturated aqueous solution of sodium chloride, dried over magnesium sulfate, and concentrated to give a brown oil (240 mg). The product, without purifying, was dissolved in a mixture (2 ml) of AcOH, H$_2$O and THF (1:1:1) with ice cooling, and was stirred for 2 hours at 0° C. To the reaction mixture was added a small amount of ether (about 10 ml), and the mixture was neutralized with a saturated aqueous solution of sodium hydrogen carbonate. The mixture was extracted with ether (100 ml). The extracts was washed with a saturated aqueous solution (5 ml×2) of sodium chloride, dried over anhydrous magnesium sulfate, and concentrated. The residue was chromatographed on a silica gel column (ethyl acetate:petroleum ether=1:2) to give ketoalcohol compound 6 (140 mg, 58.4%) as colorless oil.

IR (neat): 3400, 2925, 2850, 1740, 1710, 1440, 1020 cm$^{-1}$.

NMR ($\delta$, CDCl$_3$): 5.40 (m, 2H), 4.70 (m, 2H), 3.65 (s, 3H), 0.90 (m, 3H).

Mass (m/e): 5.48 (M=H$_2$O), 517 (M—H$_2$O—OCH$_3$), 463, 448. m/e: 517.3518 (calcd for C$_{31}$H$_{49}$O$_6$, 517.3516, M—H$_2$O—OCH$_3$).

REFERENTIAL EXAMPLE 3

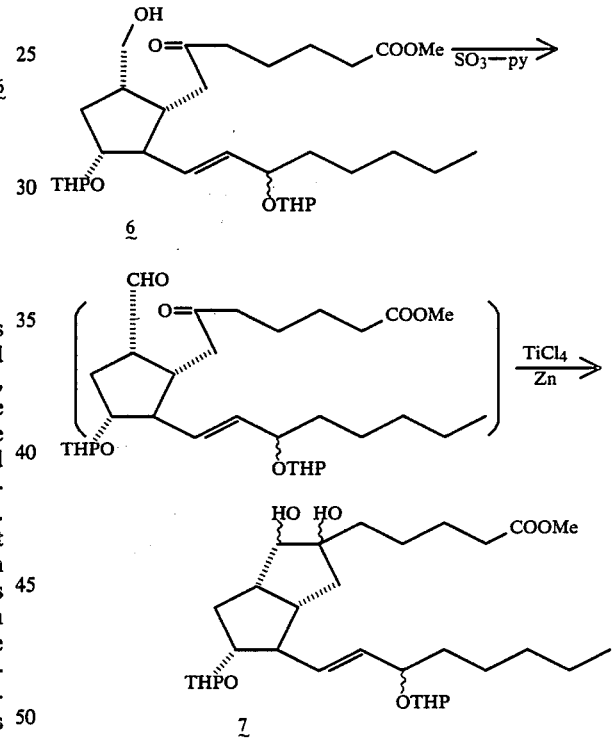

To a solution of a dry dimethylsulfoxide (DMSO, 2 ml) in a distilled triethylamine (Et$_3$N, 0.35 ml, 2.5 mmol) was added a ketoalcohol compound 6 (140 mg, 0.247 mmol), and a solution of SO$_3$-pyridine complex (Aldrich, 200 mg, 1.25 mmol) in DMSO (1 ml) was added dropwise to the mixture by a syringe at room temperature with stirring. The resulting solution was stirred for 30 minutes at room temperature, and the solution of SO$_3$-pyridine complex in DMSO (1 ml) was added dropwise. It was confirmed by TLC (ethyl acetate:petroleum ether=1:2) that the starting material disappeared. The reaction solution was diluted with ether (about 20 ml), and to the mixture were added a saturated aqueous solution (2 ml) of sodium chloride and 10% HCl (2 ml). The mixture was stirred until the organic layer became clearness. To the resulting mixture was added ether (40 ml), and the mixture was washed with 10% HCl until the water layer became acid. The mixture was neutralized with a saturated aqueous solution of sodium hydrogen carbonate, and washed with a saturated aqueous solution of sodium chloride. The organic layer was separated, dried over anhydrous magnesium sulfate, and concentrated to give a crude ketoaldehyde compound (140 mg) as a light brown oil. The product was immediately subjected to the next reaction without purifying. The product was dissolved in dry THF with ice cooling, and distilled. In the other hand, to a yellow solution of TiCl$_4$ (0.07 ml, 0.639 mmol) was added zinc powder (130 mg, 2 mmol) at once, and the mixture was stirred for 10 minutes at 0° C. to turn dark blue. To the solution was added dropwise the aforementioned solution of the ketoalhyde (140 mg) in THF, and the mixture was stirred for 1 hour at 0° C. The starting material disappeared. The reaction mixture was diluted with ether (about 30 ml), and to the mixture was added a saturated aqueous solution (about 5 ml) of potassium carbonate with cooling to stop the reaction. After the mixture was stirred sufficiently, it was extracted with ether (about 150 ml). The extract was washed with a saturated aqueous solution (5 ml×1) of sodium hydrogen carbonate and a saturated aqueous solution (5 ml×2) of sodium chloride, dried over anhydrous magnesium sulfate, and concentrated to give a crude diol compound 7 (130 mg) as a light yellow oil. The crude product was subjected to the next reaction without purifying.

IR (neat): 3420, 2910, 2850, 1735, 1140 cm$^{-1}$.

NMR ($\delta$, CDCl$_3$): 5.50 (m, 2H), 4.70 (m, 2H), 3.70 (s, 3H), 0.90 (m, 3H).

REFERENTIAL EXAMPLE 4

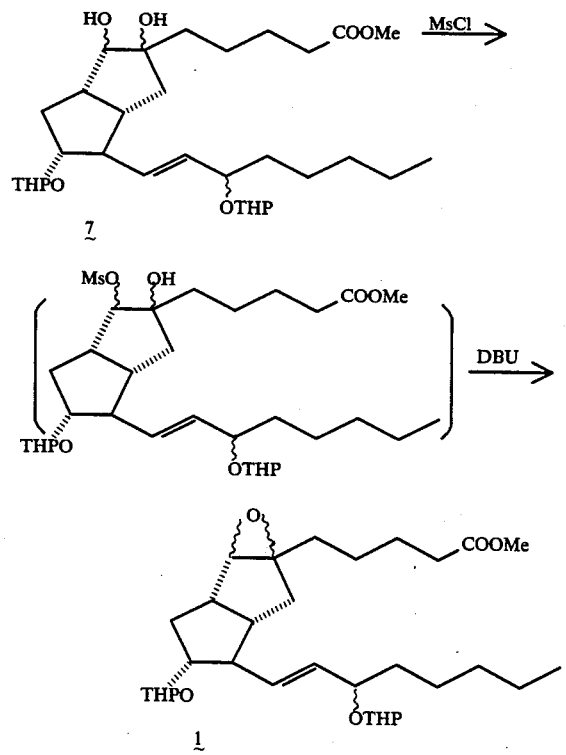

The crude diol compound 7 (112 mg, about 0.2 mmol) was dissolved in CH$_2$Cl$_2$ (1.5 ml), and cooled to −25° C. To the solution were added a distilled Et$_3$N (0.05 ml, 0.356 mmol) and methanesulfonylchloride (0.025 ml, 0.32 mmol), and the mixture was stirred for 10 minutes at −25° C. It was confirmed by TLC (ethyl acetate:petroleum ether=1:2) that the less polar product than the starting material 7 was formed. The reaction solution was diluted with a small amount of ether (about 20 ml), and a saturated aqueous solution (5 ml) of sodium chloride was added. After the cooling-instrument was removed, the solution was stirred until the organic layer became clearness. The water layer was extracted with ether (about 100 ml), and the extract was washed with a saturated aqueous solution of sodium hydrogen carbonate and a saturated aqueous solution of sodium chloride, dried over anhydrous magnesium sulfate, and concentrated to give a residue (120 mg, a light yellow oil). The residue, without purifying, was dissolved in a dry toluene (1 ml), and to the solution was added DBU (0.2 ml) at room temperature. The mixture was stirred for 2 hours at room temperature. In 30 minutes, 1 hour, 1.5 hours and 2 hours respectively after reaction started, DBU (0.1 ml) was added, but it was not confirmed by TLC that the remarkable change happen in the reaction system. The reaction solution was diluted with ether (about 20 ml), and a a saturated aqueous solution (3 ml) of sodium chloride and 10% HCl (2 ml) was added, and the mixture was stirred for a while. The resulting mixture was extracted with ether (about 80 ml). The ether layer was washed with 10% HCl until the water layer became acid. It was washed with a saturated aqueous solution of sodium hydrogen caronate and a saturated aqueous solution of sodium chloride, dried over anhydrous magnesium sulfate, and concentrated. The obtained residue was chromatographed on a silica gel column (ether:petroleum ether=1:1) to give a epoxide compound 1 (31 mg, 26.5% from 7) as a colorless oil.

IR (neat): 2925, 2850, 1735, 1440 cm$^{-1}$.

NMR ($\delta$, CDCl$_3$): 5.40 (m, 2H), 4.70 (m, 2H), 4.20–3.70 (m, 4H), 3.68 (2, 3H), 3.65–3.30 (m, 2H), 3.25 (s, 1H), 0.90 (m, 3H).

Mass (m/e): 548 (M+), 534, 503, 474, 464, 456. m/e: 548.3685 (calced for C$_{32}$H$_{52}$O$_7$, 548.3699, M+).

REFERENTIAL EXAMPLE 5

(i) Measurement of in vitro inhibitory activity of platelet aggregation

The in vitro platelet aggregation inhibiting activities of 9(0)-methano-$\Delta^{6(9)}$-prostaglandin I, obtained in Example 3 was examined by using rabbits. Blood was withdrawn from the ear vein of Japanese domestic white male rabbits weighing 2.5 to 3.5 kg. A mixture of a 3.8% trisodium citrate solution and the blood in a ratio of 1:9 was centrifuged at a speed of 1000 rpm for 10 minutes. The upper layer was separated as platelet-rich plasma (PRP). The lower layer was further centrifuged at a speed of 28000 rpm for 10 minutes. The upper layer was separated as platelet-poor plasma (PPP). The number of platelets was adjusted to 6×10$^5$/μl to 7×10$^5$/μl by diluting the PRP with PPP. 25 microliters of the test compound prepared as shown below was added in an amount of 250 microliters of PRP after the adjustment, and the mixture was pre-incubated at 37° C. for 2 minutes, and then 10 μM (final) of ADP was added. By using an aggregometer, changes in transmission were recorded.

The test compound was dissolved in ethanol to a concentration of 10 mg/ml. When its activity was measured, it was used after being diluted with phosphate buffer (pH 7.4).

The rate of inhibition of platelet aggregation was determined from the following equation.

$$\text{Inhibition rate (\%)} = \left(1 - \frac{T}{T_o}\right) \times 100$$

$T_o$: the transmittance of the system containing the phosphate buffer,

T: the transmittance of the system to which the test compound was added.

The minimum concentration of the compound which inhibited more than 50% of platelet aggregation was shown as an $IC_{50}$ value.

The results are shown in Table 1.

(ii) Measurement of the hypotensive activity

The actions of the 9(0)-methano-$\Delta^{6(9)}$-prostaglandin 1, obtained in Example 3 on the blood pressure and heart rate of rats were examined by intravenous injection under anesthesia.

Male wister rats weighing about 250 g were used. Urethane (500 mg/kg) and α-chloralose (100 mg/kg) were intraperitoneally administered to the rats. The rats were anesthetized and fixed place.

The test compound was dissolved in a small amount of ethanol and diluted with 0.05M Tris buffer saline (pH 9) to adjust the final ethanol concentration to not more than 5%. The solution was intravenously injected into the rats through a cathether inserted into the femoral vein.

The blood pressure of the rats was measured by a pressure transducer through a cathether inserted into the carotid artery of the rats. The heart rate was determined from the blood pressure pulse.

The action of the test compound on the blood pressure was expressed as the dosage ($ED_{20}$, μg/kg) of the test compound which caused a 20% lowering of the mean blood pressure before administration of the compound. The action of the test compound on the heart rate was expressed as the dosage ($ED_{10}$, μg/kg) of the test compound which caused a 10% increase of the heart rate from the heart rate before administration of the test compound.

The results are shown in Table 1. (ii) From the results obtained in (i) and (ii), the ratio ($ED_{20}/IC_{20}$) of the blood pressure lowering activity and the platelet aggregation inhibiting activity was calculated as the value of selectivity of activities. The result is shown in Table 1.

TABLE 1

| Compound | platelet aggregation inhibiting activity $IC_{50}$ (ng/ml) | blood pressure lowering activity $ED_{20}$ (μg/kg) | increase of heart rate $ED_{10}$ (μg/kg) | $ED_{20}/IC_{50}$ |
|---|---|---|---|---|
| 9(0)-methano-$\Delta^{6(9)}$-prostaglandin $I_1$ | 5.4 | 1.7 | >30 | 314 |
| $PGI_2$ | 1.6 | 0.068 | >10 | 43 |

As shown in Table 1, the compound of the present invention has a strong activity of inhibiting platelet aggregation selectively, and therefore has high selectivity of pharmacological activity.

Industrial Application

The prostacyclins of the present invention has an excellent inhibitory activity of platelet aggregation, and therefore useful for medicine such as antithrombotic drug, antiarteriousclerotic durg, and antimetastatic drug, and can be expected to be applied to atiulcer drug and antiasthma drug.

We claim:

1. Prostacyclins expressed by the following formula (1)

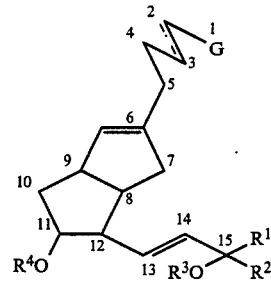

wherein a symbol ═══ between the 2-position and 3-position indicates a single bond or double bond; G indicates —$CO_2R^5$ or —$CONR^6R^7$ in which $R^5$ is a hydrogen atom, $C_1$–$C_{10}$ alkyl group, substituted or unsubstituted phenyl group, substituted or unsubstituted $C_5$–$C_8$ alicyclic group, substituted or unsubstituted phenyl($C_1$–$C_2$)alkyl group, tri($C_1$–$C_7$)-hydrocarbon-silyl group, or one equivalent cation comprising alkali metal cations or ammonium cations, $R^6$ and $R^7$ are identical or different and each represents a hydrogen atom, or $C_1$–$C_{10}$ alkyl group, or $R^6$ and $R^7$ are, together with substituted or unsubstituted five to six-membered rings, selected from the group consisting of 1-pyrrolidyl, thiazolyl, 1-piperidyl, morpholyl, piperazyl and 5,6-dihydrophenonthridyl, $R^1$ indicates a hydrogen atom, or methyl group; $R^2$ indicates an unsubstituted $C_3$–$C_8$ alkyl group, substituted or unsubstituted $C_5$–$C_8$ alicyclic group, or substituted $C_1$–$C_5$ alkyl group substituted by substituents selected from phenyl, phenoxy, $C_1$–$C_6$ alkoxy and $C_5$–$C_6$ cycloalkyl group, which substituents may be substituted; and $R^3$ and $R^4$ are identical or different, each indicating a hydrogen atom, $C_2$–$C_7$ acyl group, tri($C_1$–$C_7$)hydrocarbon-silyl group, or a group which forms an acetal linkage together with the oxygen atom of the hydroxyl group; and the substituents on the substituted phenyl groups, $C_5$–$C_8$ alicyclic group, phenyl-($C_1$–$C_2$)alkyl group, five to six-membered ring, phenoxy, $C_1$–$C_6$ alkoxy, and $C_5$–$C_6$ cycloalkyl are a halogen group, hydroxy group, $C_2$–$C_7$ acyloxy group, $C_1$–$C_4$ alkyl group which may be substituted by a halogen atom, $C_1$–$C_4$ alkoxy group which may be substituted with a halogen atom, nitrile group, carboxyl group, or $C_1$–$C_6$ alkoxycarbonyl group.

2. The prostacyclins according to claim 1, wherein G in the aforementioned formula (1) is —$CO_2R^5$ in which $R^5$ is a hydrogen atom, $C_1$–$C_{10}$ alkyl group, or cation of an alkali metal.

3. The prostacyclins according to claim 1 or 2, wherein $R^2$ in the aforementioned formula (1) is n-pentyl, 2-methyl-1-hexyl, 1-methyl-1-pentyl, cyclohexyl, or cyclopentyl.

4. The prostacyclins according to claim 1 or 2, wherein $R^3$ and $R^4$ in the aforementioned formula (1)

are identical or different and each represents a hydrogen atom, t-butyldimethylsilyl, 2-tetrahydropyranyl, acetyl, 1-methoxy-1-methylethyl, 4-(4-methoxytetrahydropyranyl), 6,6-dimethyl-3-oxa-2-oxobicyclo[3,1,0-]hex-4-yl, or dimethyl(2,4,6-tri-t-butylphenyloxy)silyl.

5. The prostacyclins according to claim 3, wherein $R^3$ and $R^4$ in the aforementioned formula (1) are identical or different and each represents a hydrogen atom, t-butyldimethyl-silyl, 2-tetrahydropyranyl, acetyl, 1-methyloxy-1-methylethyl, 4-(4-methoxytetrahydropyranyl), 6,6-dimethyl-3-oxa-2-oxo-bicyclo[3,1,0-]hex-4-yl, or dimethyl(2,4,6-tri-t-butylphenyloxy)silyl.

* * * * *